United States Patent
Carreras et al.

(10) Patent No.: US 10,350,567 B2
(45) Date of Patent: Jul. 16, 2019

(54) SERIES OF CAPSULES COMPRISING AT LEAST ONE DROP OF INTERNAL PHASE IN A DROP OF INTERMEDIATE PHASE AND MANUFACTURING METHOD THEREOF

(75) Inventors: Enric Santanach Carreras, Marseilles (FR); Yan Pafumi, Gardann (FR)

(73) Assignee: CAPSUM, Marseilles (FR)

( * ) Notice: Subject to any disclaimer, the term of this patent is extended or adjusted under 35 U.S.C. 154(b) by 255 days.

(21) Appl. No.: 13/977,510

(22) PCT Filed: Dec. 29, 2011

(86) PCT No.: PCT/EP2011/074254
§ 371 (c)(1),
(2), (4) Date: Sep. 23, 2013

(87) PCT Pub. No.: WO2012/089820
PCT Pub. Date: Jul. 5, 2012

(65) Prior Publication Data
US 2014/0011033 A1    Jan. 9, 2014

(30) Foreign Application Priority Data
Dec. 31, 2010 (FR) ..................................... 10 61404

(51) Int. Cl.
| | |
|---|---|
| *B01J 13/04* | (2006.01) |
| *B01J 13/20* | (2006.01) |
| *A61K 9/16* | (2006.01) |
| *A61K 9/48* | (2006.01) |
| *A23P 10/30* | (2016.01) |

(52) U.S. Cl.
CPC ............. *B01J 13/046* (2013.01); *A23P 10/30* (2016.08); *A61K 9/1652* (2013.01); *A61K 9/4808* (2013.01); *A61K 9/4833* (2013.01); *B01J 13/20* (2013.01); *Y10T 428/2985* (2015.01)

(58) Field of Classification Search
CPC ..... A23P 10/30; A61K 9/1652; A61K 9/4808; A61K 9/4833; B01J 13/046; B01J 13/20; Y10T 428/2985
USPC ........ 428/402-402.24, 403, 404, 407, 321.1, 428/474.4; 427/331, 389.9, 212, 427/213-213.36, 483, 256; 424/400, 408, 424/450, 451, 455, 93.7, 184.1, 497, 489, 424/501, 490, 491, 492, 493, 494, 495; 264/534, 5, 41, 4-4.7
See application file for complete search history.

(56) References Cited

U.S. PATENT DOCUMENTS

| | | | | |
|---|---|---|---|---|
| 5,330,835 | A * | 7/1994 | Kikuchi | .................. A23F 5/243 264/4.4 |
| 2006/0051329 | A1* | 3/2006 | Lee | ........................ B01F 3/0807 424/93.7 |
| 2009/0012187 | A1* | 1/2009 | Chu | ........................ A61K 9/113 516/54 |
| 2010/0136544 | A1* | 6/2010 | Agresti | .................. C12P 19/34 435/287.2 |
| 2012/0003285 | A1* | 1/2012 | Bibette | ............... A23L 1/22016 424/401 |

FOREIGN PATENT DOCUMENTS

WO    WO2010/063937    *  6/2010

* cited by examiner

*Primary Examiner* — Irina S Zemel
(74) *Attorney, Agent, or Firm* — Eric L. Lane; Green Patent Law (57) ABSTRACT

Each capsule comprises a liquid core (14) and a gelled shell (16) comprising a gelled polyelectrolyte completely encapsulating the liquid core (14) at the periphery thereof. The gelled shell (16) is suitable for retaining the liquid core (14) when the capsule (12) is immersed in a gas.

The liquid core (14) comprises an intermediate drop (18) of an intermediate phase, the intermediate phase being placed in contact with the gelled shell (16), and at least one internal drop (20) of an internal phase placed in the intermediate drop (18). The ratio of the volume of the core (14) to the volume of the gelled shell (16) is greater than 2, advantageously is greater than 50.

9 Claims, 6 Drawing Sheets

SERIES OF CAPSULES COMPRISING AT LEAST ONE DROP OF INTERNAL PHASE IN A DROP OF INTERMEDIATE PHASE AND MANUFACTURING METHOD THEREOF

The present invention relates to a series of capsules, each capsule being of the type comprising:
a liquid core,
a gelled shell comprising a gelled polyelectrolyte completely encapsulating the liquid core at the periphery thereof, the gelled shell is suitable for retaining the liquid core when the capsule is immersed in a gas.

Such capsules, which comprise a liquid core encapsulated a gelled shell that is substantially solid, present applications in many technical fields.

Thus, in the food industry, these capsules are used to contain various additives that improve the properties of a food product, such as taste or shelf life.

In the pharmaceutical industry and in the cosmetics industry, the aforementioned capsules are in particular filled with products that are biologically or cosmetically active. They are mainly used in particular for protecting their content and controlling the release of the product that they contain.

Such capsules are also used in applications in biochemistry for immobilising cells in bioreactors or as artificial cells in implants.

In all these applications, the capsule shells are usually made of a material that is biocompatible with the human body. For this purpose, it is a known technique to form the shell with polymers such as polysaccharides, which are biocompatible, biodegradable and in most cases non-toxic. These polymers can advantageously pass from a liquid state in solution to a significantly more viscous state to form a gel ensuring the mechanical retention of liquid contained in the capsule.

In order to form such capsules, the patent application WO 2010/063937 describes a method in which capsules having an outer shell formed of alginate are formed by coextrusion of drops at the outlet of a double wall. The drops fall in a volume of air, and then are immersed in a gelling solution to carry on with the gelation of the shell. Hence, the shells obtained thus have a narrow thickness.

Such a method makes it possible to encapsulate in a simple and effective way a wide variety of liquid products.

Such a method has some limitations depending on the nature of the liquid to be encapsulated. In particular, it is tedious to encapsulate preparations that interact with the liquid containing the polyelectrolyte liquid suitable for the gelation. Thus, solutions containing ions such as calcium or other divalent ions, solutions containing a high concentration of alcohol, for example greater than 30% by volume, or solutions with a pH lower than 4.5, are more difficult to encapsulate using the method described in the document WO 2010/063937.

An object of the invention is thus to obtain capsules containing a wide variety of liquid and which nevertheless remain easy to form, all while having a shell of narrow thickness in order to ensure the effective disintegration of the capsule when the liquid contained in the capsule should be released.

To this end, the invention relates to a series of capsules of the aforementioned type, characterised in that:
the liquid core comprises an intermediate drop of an intermediate phase, the intermediate phase being placed in contact with the gelled shell, and at least one internal drop of an internal phase placed in the intermediate drop, the ratio of the volume of the core to the volume of the gelled shell being greater than 2, advantageously being less than 50.

The series of capsules according to the invention may comprise one or more of the following characteristic features, considered alone or according to all combinations technically possible:
the ratio of the volume of the core to the volume of the gelled shell is between 5 and 10;
the thickness of the gelled shell is less than 500 microns, and is advantageously greater than 10 microns;
each internal drop is placed completely away from the gelled shell, the intermediate phase being interposed between the or each internal drop and the gelled shell;
the or each internal drop has a volume greater than 0.5% and advantageously less than 60% of the volume of the core;
the maximum transverse dimension of the or each internal drop is greater than 150 micrometers, advantageously greater than 300 micrometers;
each capsule comprises at least two internal macroscopic drops disposed in the intermediate drop, each internal macroscopic drop comprising an internal phase, each capsule advantageously comprising less than twenty internal macroscopic drops disposed in the intermediate phase, advantageously less than five internal macroscopic drops disposed in the intermediate phase, advantageously two internal macroscopic drops disposed in the intermediate phase; and
each capsule comprises at least two internal macroscopic drops with internal phases having distinct compositions;
each intermediate drop is formed of an oily intermediate phase, the internal phase forming each internal drop being aqueous;
the intermediate drop is viscous or gelled;
the intermediate drop contains a polymer and/or a silicone based copolymer;
the intermediate drop contains between 60% and 90% of a silicone based crosspolymer solution and between 10% by weight and 40% by weight of polydimethylsiloxane,
the intermediate drop contains solid particles, advantageously particles of pearl.

The invention also relates to a method for manufacturing a series of capsules, each capsule comprising a liquid core and a gelled shell completely encapsulating the liquid core, the method comprising of the following steps:
separate conveying in a double wall of an internal phase intended to form the liquid core and a first solution containing a polyelectrolyte liquid capable of gelling intended for forming the gelled shell;
formation at the outlet of the double wall of a series of liquid bodies including one drop of intermediate phase coated with a peripheral film formed by a first solution;
detachment of each liquid body away from the double wall and falling of each liquid body in a volume of air;
immersion of each liquid body into a gelling solution containing a reagent capable of reacting with the polyelectrolyte of the film in order to make it pass from a liquid state to a gelled state and thereby form the gelled shell;
recovery of the capsules formed with a ratio of the volume of the core to the volume of the shell being greater than 2, advantageously less than 50;
the method comprising a step of forming at least one internal macroscopic drop of one internal phase in the intermediate phase, each liquid body formed at the outlet of the double wall comprising one internal macroscopic drop of an internal phase disposed in the intermediate phase.

The method of manufacture according to the invention may comprise of one or more of the following characteristic features, taken individually in accordance with all combination s technically possible:

- each intermediate drop of the intermediate phase formed at the outlet of the double wall comprises at least two internal drops placed in the intermediate phase;
- the step of formation includes injection of the internal phase in a current of the intermediate phase flowing in the double wall so as to form internal macroscopic drops;
- the injection of the internal phase is performed through an internal duct arranged in the double wall, the internal duct opening advantageously withdrawn from the outlet of the double wall;
- the first solution contains at least one surfactant prior to its contact with the intermediate phase,
- the method includes the adjusting of the rate of injection of the internal phase in the intermediate phase relative to the rate of injection of the intermediate phase in order to adjust the number of internal macroscopic drops present in each intermediate drop formed at the outlet of the double wall.
- each intermediate drop is formed from an oily intermediate phase, the internal phase forming each internal drop being aqueous;
- the intermediate drop is viscous or gelled;
- the intermediate drop contains a polymer and/or a silicone based copolymer;
- the intermediate drop contains between 60% and 90% of a silicone based crosspolymer solution and between 10% by weight and 40% by weight of polydimethylsiloxane;
- the intermediate drop contains solid particles, advantageously particles of pearl.

The invention will be better understood upon reading the description which follows, given by way of example, and with reference being made to the accompanying drawings, in which.

Figure 1:
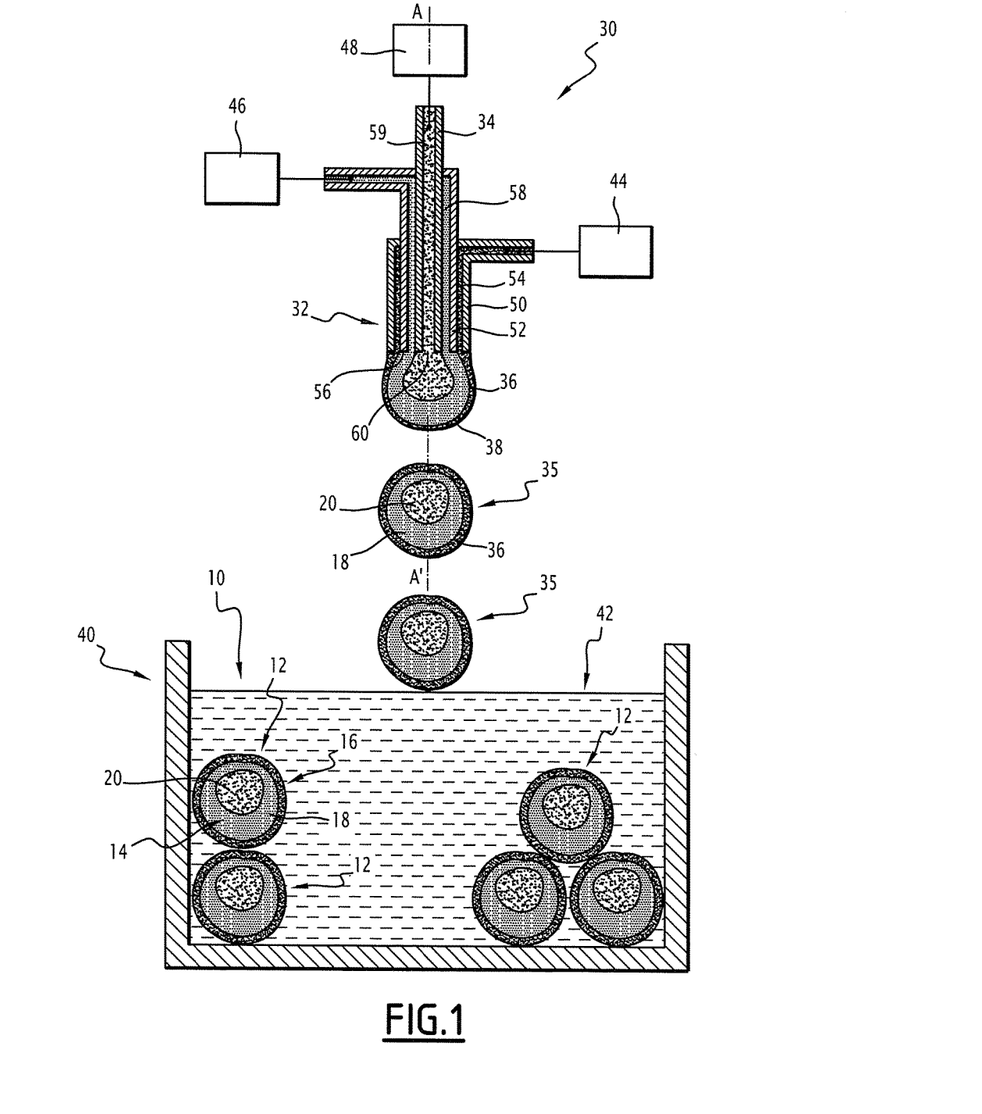
FIG. 1 is a schematic view, taken in partial cross section of a first apparatus for forming a series of capsules according to the invention, during a method for manufacturing this series of capsules.

A first series 10 of capsules 12 according to the invention is illustrated in FIG. 1.

Each capsule 12 comprises a liquid core 14 and an external gelled shell 16 encompassing the entire external surface of the liquid core 14 so as to hold the liquid core 14, in particular when the capsule is immersed in a volume of gas.

In this example, each capsule 12 has a substantially spherical shape and an outer diameter greater than 0.5 mm, advantageously less than 10 mm. The diameter of each capsule 12 is in particular between 1 mm and 5 mm. This diameter is advantageously measured over at least seven capsules by means of using the image processing software "Image J", based on a photograph of the capsules 12 taken in top view with a digital camera.

The capsules 12 in particular have a monodisperse distribution. In this respect, the size polydispersity of the capsules 12, as measured by the coefficient of variation C, constituted by the ratio of the standard deviation to the mean is less than 3%, and in particular between 1% and 2%.

This ratio can be measured, for example on the basis of the diameters measured over at least seven capsules by means of using the image processing software "Image J", based on a photograph of the capsules 12 taken in top view with a digital camera.

Alternatively, the mass polydispersity of the capsules can be calculated, based on at least fifty measurements of the mass of fifty capsules 12 carried out by means of using a scale of the type Mettler-Toledo with a precision of 0.1 mg.

As shown in FIG. 1, the core 14 includes an intermediate drop 18 formed from a base of an intermediate phase and at least one internal macroscopic drop 20 placed in the intermediate drop 18 and formed of an internal phase that is substantially immiscible with the intermediate phase.

Each capsule 20 has one single intermediate drop 18.

The intermediate phase is made, for example from a base of an aqueous or oily solution.

The flow viscosity of the intermediate phase, measured under the conditions applied during the formation of the capsules 12, is substantially lower, for example at least 5% lower than the viscosity of the first solution intended to form the shell 16, as will be discussed further here below.

This viscosity at shear gradients characteristic of flows applied during the manufacture of such capsules is for example, measured by means of using a stress rheometer, or deformation, imposed at the production temperature, 25° C. for example. For the measurements a cone-plate geometry of diameter between 10 and 50 mm and a cone angle of 2° maximum will be used.

The intermediate drop 18 is advantageously liquid. By way of a variant, the intermediate drop 18 is made from a base of a thixotropic intermediate phase, which is in the liquid state and destructured as it flows, but which is substantially solid or gelled upon standing.

The expression "liquid when it flows" is understood to mean that the behaviour of the intermediate phase is viscous, that is to say the deformation of the material depends not only on the applied stress but also on the period during which this constraint is applied. One way to characterise this behaviour is by doing a flow test by using a rheometer on the sample, a characteristic value of flow stress brought into play during the manufacture is applied and deformation is plotted versus time (data obtained with the rheometer software). If the curve has a non-zero slope with long time (more than 30 seconds), the intermediate phase may be considered as being liquid. If this slope is zero, the intermediate phase can be considered as being solid.

The expression "solid or gelled upon standing" is understood to mean that the behaviour of the solid or gelled intermediate phase upon standing, that is to say the deformation of the material depends only the stress applied. One way to characterise this behaviour is by doing a flow test by using a rheometer on the sample, a constraint characteristic of those experienced by the capsule upon standing versus time (data obtained with the software for rheometer) is applied. If the curve has a zero slope at long times (more than 30 seconds), the intermediate phase may be considered as being solid. If the slope is not zero, the intermediate phase may be considered as being liquid.

Alternatively, the intermediate drop 18 is gelled. In this case, the intermediate drop 18 is for example formed by gelation of a gelling product obtained by a temperature change, in particular by a temperature decrease of at least 10° C. By way of a variant, the gelation is obtained in the presence of ions, other molecules or certain conditions of pH or ionic strength.

The intermediate drop 18 may include one or more edible, cosmetics, or pharmaceutical active ingredients. By way of a variant, the intermediate drop 18 includes a cosmetic active ingredient such as sodium hyaluronate or other hydrating/repairing molecules, of vitamins, enzymes, anti-aging-, anti wrinkle active ingredients, protective/antiradical active ingredients, antioxidants, soothing, softening, anti irritants, tensor/smoothing, emollients, slimming, anti cellulite, firming, sheathing, draining, anti-inflammatory, skin bleaching, whitening, tanning, exfoliating, cell renewal stimulating and skin microcirculation stimulating, absorbent or UV filtering, and anti dandruff active ingredients.

In another variant, the intermediate drop comprises a biologically active product advantageously chosen from anticoagulants, anti-thrombogenics, anti-mitotic agents, antiproliferative agents, anti-adhesion, anti-migration, cell adhesion promoters, growth factors, antiparasitic molecules, anti-inflammatories, angiogenics, angiogenesis inhibitors, vitamins, hormones, proteins, antifungals, antimicrobial molecules, antiseptics or antibiotics.

The intermediate drop 18 may also include excipients, such as thickeners or rheology modifiers. These thickeners are for example polymers, cross-polymers, microgels, gums or proteins, polysaccharides, celluloses, polysaccharides, silicone based polymers and copolymers, colloidal particles (silica, clays, latex . . . )

Examples of intermediate phase are in particular solutions containing include:

| | |
|---|---|
| Example 1 of intermediate phase: | 1% high molecular weight sodium hyaluronate, 99% ultra pure water. |
| Example 2 of intermediate phase: | 2% lambda carrageenan, 98% ultra pure water. |
| Example 3 of intermediate phase: | 0.5% sodium hyaluronate 0.3% gellan gum, 2.2% active ingredients, 97% ultra pure water. |
| Example 4 of intermediate phase:. | 100% solution of silicone based crosspolymer in low viscosity polydimethylsiloxane (6 cst) |

The volume of the intermediate drop 18 represents in particular more than 40% of the total volume of the core 14.

This volume is for example between 2.5% and 80% of the total volume of the core.

Advantageously, the intermediate drop 18 is completely interposed between the or each internal drop 20 and the shell 16. Thus, the entire internal surface of the shell 16 is in contact with the intermediate drop 18 so that the intermediate drop 18 holds the or each internal drop 20 completely away from the shell 16.

As mentioned here above, the core 14 contains at least one internal drop 20 in the intermediate drop 18, and advantageously less than twenty internal drops 20 placed in the drop 18.

Thus, the number of internal drops 20 in each intermediate drop 18 is for example between 2 and 20, and is in particular less than 5, for example between 1 and 4, and in particular is equal to 1, 2, 3 or 4.

The Internal drops 20 are macroscopic. Thus, the maximum transverse dimension of each drop 20, given by its diameter, when it is spherical, is greater than 150 micrometers, and in particular is greater than 300 micrometers. These dimensions are measured by the method described here above.

The minimum volume of at least one internal drop 20 is thus greater than 0.5% of the volume of core 14.

The sum of the volumes of the or each internal drop 20 is thus between 0.5% and 60% of the total volume of the core, in particular between 1% and 30% of the volume of the core.

In the example shown in FIG. 1, each capsule 12 has a single internal drop 20 with a volume higher than 10% of the volume of the core and in particular between 20% of the volume of the core and 80% of the volume of the core.

Each internal drop 20 advantageously has a spherical shape. By way of a variant, the shape of the internal drop 20 is different from a spherical shape, for example elliptical or lenticular.

The internal phase constituting the internal drops 20 is substantially immiscible with the intermediate phase constituting the intermediate drops 18.

When the intermediate phase is aqueous, the internal phase is oily, and conversely when the intermediate phase is oily, the internal phase is aqueous.

The internal phase contains for example a first product advantageously selected from a biologically active product, a cosmetic product or a comestible product suitable to be consumed.

The internal phase is thus constituted by a first pure liquid product, or by a solution of the or each first product in a liquid solvent, or by a dispersion such as an emulsion or a suspension of each first product in a liquid.

When the first product is a biologically active product, it is advantageously chosen from anticoagulants, anti-thrombogenic-, anti-mitotic agents, anti-migration-, anti-proliferation-, anti-adhesion-, anti-migration agents, cellular adhesion promoters, growth factors, antiparasitic molecules, anti-inflammatories, angiogenics, angiogenesis inhibitors, vitamins, hormones, proteins, antifungals, antimicrobial molecules, antiseptics or antibiotics. It may also be a cosmetic active ingredient such as sodium hyaluronate or other hydrating/repairing molecules, vitamins, enzymes, anti-wrinkle-, anti-aging active ingredients, protective/antiradicals, antioxidants, soothing agents, softeners, anti irritants, tensor/smoothers, emollients, slimming, anti-cellulite, firming, sheathing, draining, anti-inflammatories, skin bleaching agents, whitening, tanning, exfoliating, cell renewal stimulating—and skin microcirculation stimulating-, absorbent or UV filtering-, anti dandruff agents.

By way of a variant, the liquid core 12 contains reagents such as proteins or reagents intended to form a bioreactor, or to form artificial cells for implants.

A cosmetic product that may be contained in the core, for example, is cited in Council Directive 93/35/EEC dated 14 Jun. 1993. This product is for example a cream, an emulsion, a lotion, a gel and an oil for the skin (hands, face, feet, etc.), a foundation (liquid, paste), a preparation for baths and showers (salts, mousses, oils, gels, etc.), a hair care product (hair dyes and bleaches), a cleaning product (lotions, powders, shampoos), a hair maintenance product (lotions, creams, oils), a hair styling product (lotions, lacquers, glosses), a shaving product (creams, foams, lotions, etc.), a product intended to be applied on the lips, a solar protection product, a sunless tanning product, a product for skin whitening, an anti-wrinkle product.

Comestible products suitable to be consumed by humans or by animals are advantageously pureed vegetables or fruits such as mango puree, mashed pear, coconut puree, cream of onions, leeks, carrots, or other preparations that may mix several fruits and vegetables. By way of a variant, they are oils such as cooking oil of various types like olive oil, soybean oil, grape seed oil, sunflower oil or other oils extracted from vegetables.

The viscosity of the internal phase forming the internal drop 20 is for example less than 10% of the viscosity of the intermediate phase at characteristic shear gradients that are put into play during the process of formation of the drops, which is a viscosity of about 1000 mPa·s. This viscosity at shear gradients characteristic of flows that are put into play during the manufacture of such capsules is measured by means of using a stress rheometer or deformation, imposed at the production temperature, 25° C. for example. For the measurements a cone-plate geometry of diameter between 10 and 50 mm and a cone angle of 2° maximum will be used.

The gelled shell 16 is formed by a single layer of a homogeneous material.

The gelled shell 16 of the capsules 12 according to the invention comprises a gel containing water and at least one polyelectrolyte reactive with multivalent ions. According to the invention, the shell 16 may also contain a surfactant.

The expression "polyelectrolyte reactive with multivalent ions" is understood to mean, for the purposes of the present invention a polyelectrolyte capable of passing from a liquid state in an aqueous solution to a gelled state upon coming into contact with a gelling solution containing multivalent ions such as ions of an alkaline earth metal chosen, for example from among calcium ions, barium ions, magnesium ions.

In the liquid state, the individual chains of polyelectrolyte are substantially free to flow against each other. An aqueous solution of 2% by weight of polyelectrolyte then has a purely viscous behaviour at the shear gradients characteristic of the method of shaping. The viscosity of this solution at zero shear is between 50 mPa·s and 10000 mPa·s advantageously between 3000 mPa·s and 7000 mPa·s. This viscosity at shear gradients characteristic of flows that are put into play during the manufacture of the capsules is for example measured by means of using a stress rheometer or deformation imposed at the production temperature, 25° C. for example. For the measurements a cone-plate geometry of diameter between 10 and 50 mm and a cone angle of 2° maximum will be used.

The individual chains of polyelectrolyte in the liquid state advantageously present a molar mass greater than greater than 65000 g/moles.

In the gelled state, the individual chains of polyelectrolyte form, with the multivalent ions, a coherent three dimensional network that holds the liquid core and prevents its flow. The individual chains are held against each other and cannot flow freely relative to each other. In this state, the viscosity of the gel formed is infinite. In addition, the gel has a threshold shear stress. The yield stress is greater than 0.05 Pa. The gel also has a modulus of elasticity that is non-zero and greater than 35 kPa.

The three-dimensional polyelectrolyte gel contained in the shell 14 traps water and the surfactant agent when present. The mass content of the polyelectrolyte in the shell 12 is for example between 0.5% and 5%.

The polyelectrolyte is preferably a biocompatible polymer harmless to the human body. For example it is produced biologically.

Advantageously, it is chosen from among polysaccharides, synthetic polyelectrolytes that are acrylates based (polyacrylate of sodium, lithium, potassium or ammonium, or polyacrylamide), synthetic polyelectrolytes that are sulfonates based (poly (styrene sulfonate) of sodium, for example). More specifically, the polyelectrolyte is selected from an alkaline earth alginate, such as sodium alginate or potassium alginate, a gellan or pectin.

Alginates are produced from brown seaweed called "laminar" designated by the term "sea weed."

Such alginates advantageously have an α-L-guluronate content greater than about 50%, preferably greater than 55%, or even greater than 60%.

The surfactant is advantageously an anionic surfactant, a nonionic surfactant, a cationic surfactant or a mixture thereof. The molecular weight of the surfactant is between 150 g/mol and 10,000 g/mol, preferably between 250 g/mol and 1500 g/mol.

Where the surfactant is an anionic surfactant, for example it is selected from an alkyl sulfate, an alkyl sulfonate, an alkylaryl sulfonate, an alkali alkylphosphate, a dialkylsulfosuccinate, an alkaline earth saturated or unsaturated fatty acid salt. These surfactants advantageously have at least one hydrophobic hydrocarbon chain having a carbon number greater than 5, or 10 and at least one hydrophilic anionic group, such as a sulfate, a sulfonate or a carboxylate bound to one end of the hydrophobic chain.

In the event the surfactant is a cationic surfactant, it is for example selected from alkylpyridinium halide salts or alkylammonium salts such as chloride or bromide of n-ethyldodecylammonium, chloride or bromide of cetylammonium (CTAB). These surfactants preferably have at least one hydrophobic hydrocarbon chain having a carbon number greater than 5, or 10 and at least one hydrophilic cationic group, such as a quaternary ammonium cation.

Where the surfactant is a nonionic surfactant, it is for example selected from polyoxyethylene derivatives and/or polyoxypropylene fatty alcohols, fatty acids or alkylphenols, arylphenols, or from among alkyl glucosides, polysorbates, cocamides.

The surfactant mass content in the shell is greater than 0.001% and preferably greater than 0.1%.

In this example, the shell 14 is made up exclusively of polyelectrolyte surfactant when it is present, and water. The sum of the contents by weight of polyelectrolyte, a surfactant, and water is equal to 100%.

The shell 16 is thin. To this end, the volume ratio $R_v$ of the volume of the core to the volume 14 of the shell 16 is greater than 2, and in particular is greater than 5. This ratio $R_v$ is advantageously less than 50.

The $R_v$ ratio is for example between 5 and 10.

Thus, the thickness of the shell 16 is in particular less than 0.3 mm, and is for example between 0.025 mm and 0.1 mm.

As shown in FIG. 1, the shell 16 has a suitable mechanical strength, especially when placed in a liquid such as water or gas.

Thus, the shell 16 enables the capsule 10 to resist shear stresses and compression forces. In particular, the maximum force of compression strength of the capsules is preferably greater than 40 mN, in particular more than 90 mN and in some cases may be greater than 200 mN, for example between 400 mN and 600 mN.

Thus, for an intermediate phase that is carrageenan based, the force is of the order of 50 mN, in an intermediate phase that is sodium hyaluronate based, the force may be between 100 and 150 mN, for a vegetable oil, the force may be for example, between 150 and 200 mN and for a crosspolymer, the force is between 400 and 600 mN.

This maximum resistance to compressive forces is measured by the following method.

The capsule is deposited on a precision balance using a piston which advances at a controlled rate (of the order of 2 mm/min). The balance is connected to a computer with software that records the mass as a function of time. Mass as recorded increases as the piston compresses the capsule until the capsule bursts.

Mass measured at maximum is multiplied by the acceleration of gravity, to obtain the corresponding force.

As has been seen above, the shell 16 completely covers the core 14, in a manner such that the intermediate drop 18 and the or each internal drop 20 is completely confined within the shell 16.

The series 10 of capsules 12 is advantageously manufactured by a process implemented in a device 30 shown in FIG. 1.

As shown in this figure, the apparatus 30 includes a double external wall 32 and an internal pipe 34 disposed within the double wall 32 so as to co-extrude a series of liquid bodies 35. Each liquid body 35 comprises an intermediate drop 18 containing at least one internal drop 20, the intermediate drop 18 being coated with a film 36 of a first solution 38 of ungelled polyelectrolyte intended for forming the shell 16 after gelation.

The apparatus 30 further comprises an assembly for gelling of the film 36, formed in this example by a gelation bath 42 disposed under the double wall 32, away therefrom, and a bath for rinsing and storage (not shown).

The apparatus 30 further comprises the means 44 for feeding the first solution 36 in the double wall 32, the means 46 for feeding the intermediate phase in the double wall 32 and the means 48 for feeding the internal phase in the internal pipe 34.

In this example, the double wall 32 comprises an external tube 50 and an intermediate tube 52 disposed co-axially in the external tube 50. The external tube 50 and the internal tube 52 define between them an external annular flow chamber 54 for circulation of the first solution 38. The external annular chamber 54 is connected upstream to the means 44 for feeding the first solution.

The external tube 50 and the internal tube 52 extending along a vertical axis A-A'. They open downwardly through an opening 56 for formation of each liquid body 35.

The internal pipe 34 is disposed in the intermediate tube 52. In this example, the internal pipe 34 is mounted co-axially within the tube 52 along the axis AA'. It defines, with the intermediate tube 52, an intermediate annular chamber 58 connected upstream to the means 46 for feeding the intermediate phase.

The internal pipe 34 further defines interiorly a lumen 59 for circulation of the internal phase connected upstream to the means for feeding the internal phase 48.

In this example, the lumen 59 of the pipe 34 opens via a downstream opening 60 for distribution of the internal phase which is situated substantially at the same level as the opening 56 for drop formation.

The angle formed by the local axis of the internal pipe 34, taken at the downstream opening 60 and of the internal tube 52, taken at the same opening may be between 0° and 90°.

Similarly, the intermediate annular chamber 58 opens at the same level as the opening 56.

The feeding means 44, 46, 48 each comprise for example a syringe pump, a peristaltic pump or another pressure generating flow controlling system such as a pressure pot coupled with a flow meter and a flow control system.

A first method of manufacturing a series of capsules 12 according to the invention, implemented in the apparatus 30, will now be described.

The method comprises a step of forming at least one drop of internal phase 20 in the intermediate phase, and then a step of forming a liquid body 35 consisting of an intermediate drop 18 of the intermediate phase coated with a film 36 of a first solution 38 by coextrusion in the apparatus 30.

The method then comprises a step 35 of the fall of the body through a volume of air, and a step of dipping the body 35 in the gelling bath 42, followed by a step of rinsing/storage in a rinsing bath.

Initially, the first solution 38 containing the polyelectrolyte to be gelled, the solution of the intermediate phase and the solution of the internal phase are prepared and introduced respectively in the means 44 for feeding the first solution 38, in the means 46 for feeding the intermediate phase and in the means 48 for feeding the internal phase.

Then, the means 44, 46, 48 are activated for continuously conveying from the internal phase in the lumen 59 of the pipe 34, from the intermediate phase in the intermediate annular chamber 58 and 38 from the polyelectrolyte solution to be gelled in the external annular chamber 54.

In the first method according to the invention, as illustrated in FIG. 1, the drop 20 of the internal phase present in the intermediate phase is formed at the same time as the drop of the intermediate phase 18 covered by the film 36 of solution 38. This simultaneous formation takes place directly at the outlet of the double wall 32, at the opening 56.

The respective flow rates of internal phase, of the intermediate phase, and polyelectrolyte solution to be gelled are chosen according to the respective dimensions of the internal drop 20, the external drop 18 and the desired shell 16 and the number of internal drops 20 in each external drop 18.

Thus, the relative and independent adjustment of flow rates fed make it possible to adjust the thickness of the shell 16, and the relative size of the first drop 18 and of the or each second drop 20.

At the opening 56, a liquid body 35 substantially spherical comprised of an intermediate drop 18 containing an internal drop 20, coated with a solution film 38 is formed progressively.

The film 36 of solution 38 completely encompasses the intermediate drop 20. In addition, the polyelectrolyte contained in the solution 38 is held in its non gelled liquid state.

When the weight of the body 35 is greater than its restraining force by capillarity on the double wall 32, the body 35 is detached from the double wall 32 and falls into the gelation bath 42 by gravity, through a volume of air. The film 36 of solution to be gelled 38 then enters into contact with the gelling solution contained in the bath 42.

Upon contact multivalent ions coming from the gelling reagent, the individual chains of polyelectrolyte present in the solution 38 are connected to each other to form a cross linked network that traps the water and optionally the surfactant contained in the solution 38.

A gelled shell 16 as defined above and capable of retaining the liquid core 14 is thus produced. The shell 16 has an appropriate mechanical strength, that is to say, that it is capable of completely surrounding the liquid core 14 and of retaining the liquid present in the core 14 to prevent it from spreading through the shell 16, even when the capsule is disposed in a gas such as ambient air.

Then another body 35 is formed at the lower end of the double wall 32 and the steps described above are reproduced for this body 35.

Once the series 10 of capsules 12 is formed, they are transferred to the rinsing bath in view of their storage. The capsules 12 thus formed are thus store in a tight fashion the various compounds such as biologically active materials, proteins, cosmetic or edible products intended for consumption by humans or animals.

When using the capsules 12 the shell 16 is broken by shearing, by mechanical crushing, or possibly by chelation with multivalent ions of a suitable salt such as EDTA, in the case where calcium ions are used to form the gel of the shell. This rupture makes it possible to recover both the intermediate phase present in the intermediate drop 18 and the internal phase present in the internal drop 20.

Figure 2:
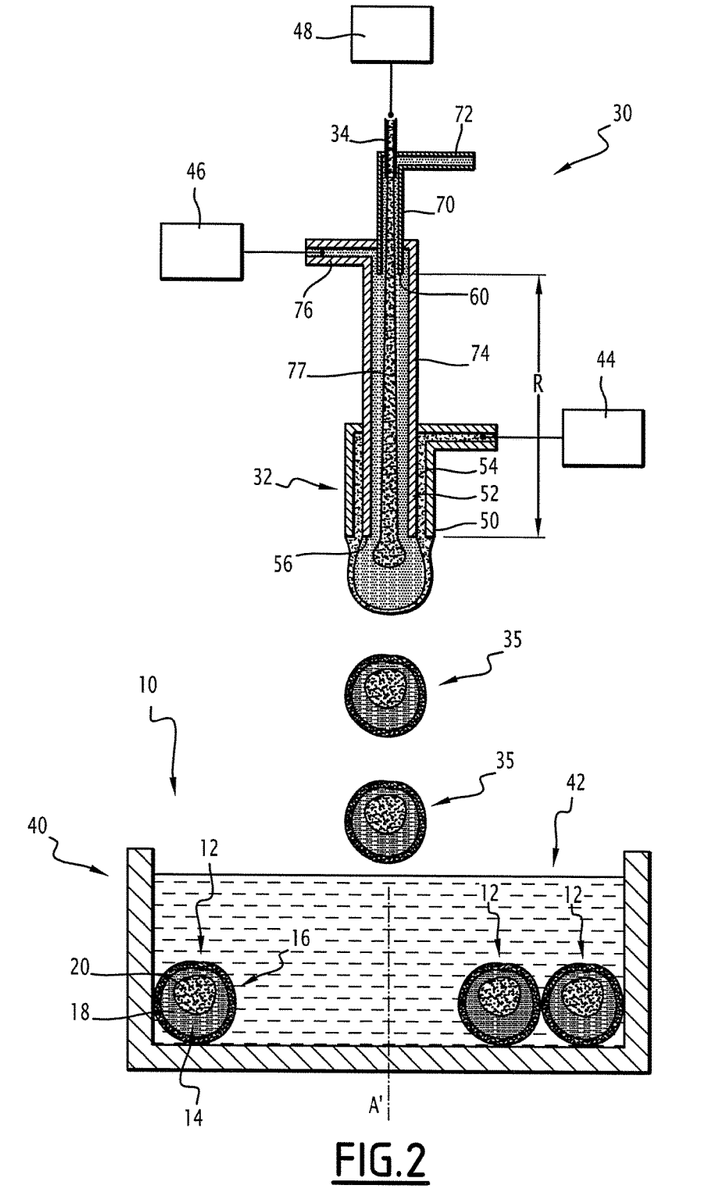
FIG. 2 is a view that is similar to FIG. 1 for a second apparatus for forming a second set of capsules according to the invention.

A variant of the apparatus 30 is depicted in FIG. 2. Unlike the apparatus 30 described in FIG. 1, the lower end of the internal pipe 34 is axially disposed away from the lower end of the internal tube 52 and from the opening 56, inside the internal tube 52.

Thus, the downstream opening 60 is offset axially relative to the opening for forming 56 of the liquid body 35.

Referring to FIG. 2, the withdrawal R of the internal pipe 34 conveying the intermediate phase in the internal tube 52, that is to say the distance, taken along the axis A-A', between the opening downstream 60 and the opening 56 for drop formation is between 10 times and 1000 times, for example between 50 times and 500 times the diameter of the internal pipe 34, taken at the downstream opening 60.

Moreover, the internal tube 52 includes an upstream portion 70 provided with an upstream inlet 72 for injection of the intermediate phase and a downstream portion 74 provided with a downstream inlet 76 for injection of the intermediate phase.

The upstream portion 70 has a smaller section than the downstream portion 74. It opens into the downstream section 74 along the axis A-A'.

The internal pipe 34 opens into the upstream portion 70, downstream of the inlet 72.

A second method for the manufacture of capsules 12 by means of using the apparatus 30 shown in FIG. 2 will now be described.

In this method, a continuous axial jet 77 of the internal phase is projected in the intermediate phase from the internal pipe 34 through the upstream portion 70 and the downstream portion 74 of the intermediate tube 52 until the opening for formation of drops 56.

As in the first method described here above, the internal drops 20 are formed simultaneously with the external drops 18 intended for receiving them, at the lower end of the double wall 32.

Figure 3:
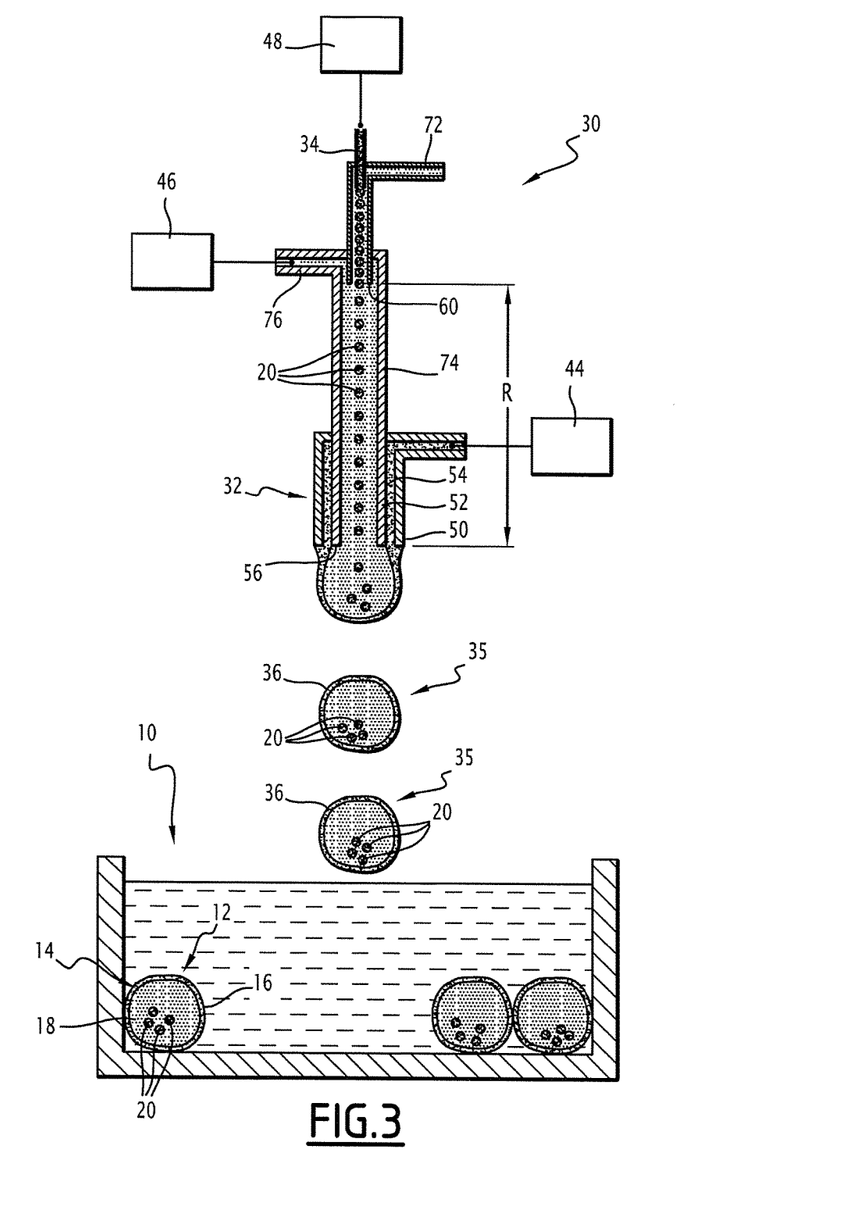
FIG. 3 is a view similar to FIG. 1 of a third apparatus for forming a third set of capsules according to the invention.

In the third method shown in FIG. 3, the step of formation of the internal drops 20 takes place within the internal tube 52, before the step of formation of the intermediate drops 18 and of each body 35.

In this method, a train of internal drops 20 is formed in the intermediate phase at the outlet of the downstream opening 60. The internal drops 20 flow within the intermediate phase 52 circulating in the tube. Then, at least one internal drop 20 is introduced into each intermediate drop 18 during the formation of the intermediate drop 18 at the outlet of the annular chamber 54.

In the example shown in FIG. 3, the series 10 of capsules 12 contains a plurality of internal drops 20 placed in each intermediate drop 18.

The number of internal drops 20 in each intermediate drop 18 is for example between 2 and 20, and is in particular less than 5 and for example equal to 2, 3 or 4.

In this example, all the internal drops 20 are identical in composition, as well as in size. In addition, the number of internal drops 20 per capsule 12 is identical for all the capsules 12.

Figure 4:
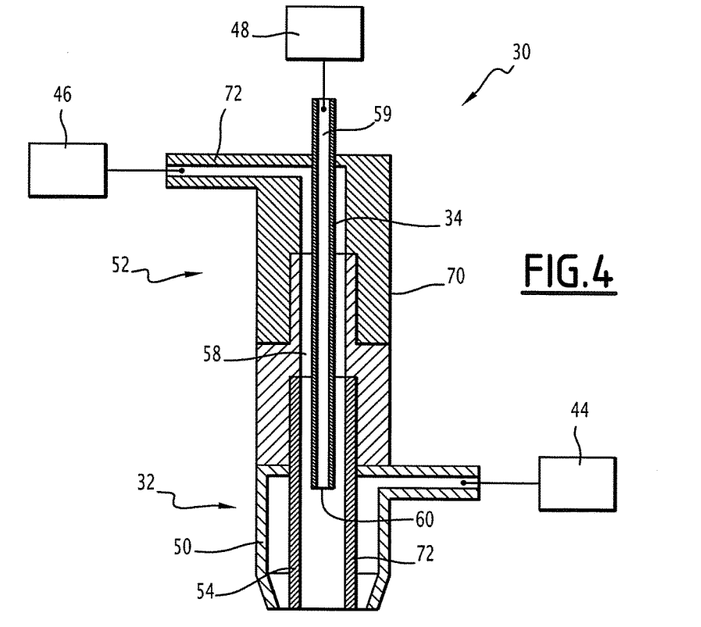
FIG. 4 is a view similar to FIG. 1 for a fourth apparatus for forming a fourth series of capsules according to the invention.

In the variant of the apparatus 30 shown in FIG. 4, and in contrast to the apparatuses 30 shown in FIGS. 2 and 3, the internal tube 52 includes a single inlet 72 for feeding the intermediate phase. The downstream opening 60 opens downstream of the inlet for injection 72 of the intermediate phase and upstream and spaced axially away from the opening 56 for drop forming.

Figure 5:
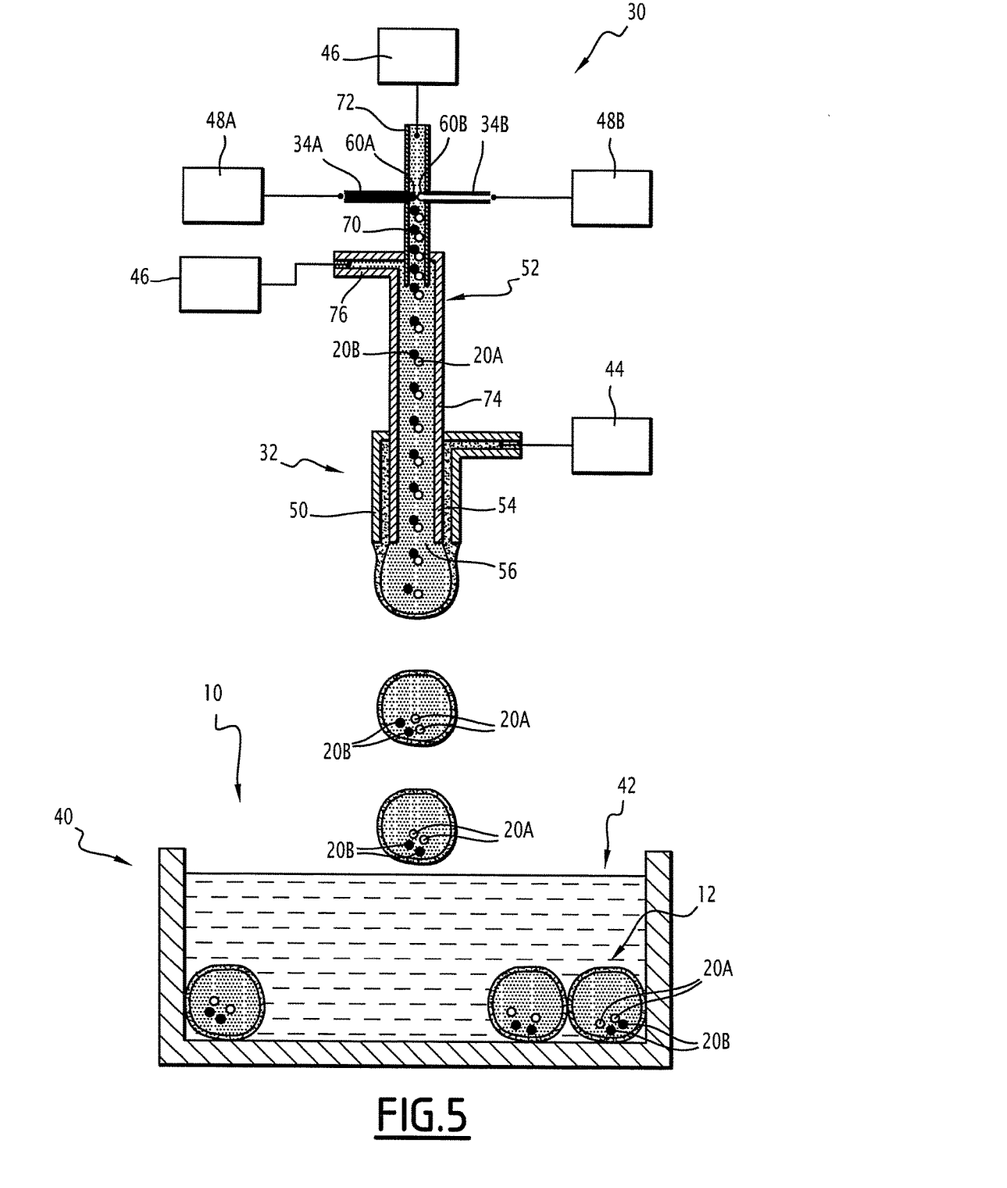
FIG. 5 is a view similar to FIG. 1 of a fifth apparatus for forming a fifth set of capsules according to the invention.

The apparatus 30 shown in FIG. 5, differs from that shown in FIG. 3 in that it comprises two internal pipes 34A, 34B that are separate, respectively connected upstream to a first means 48A for feeding a first internal phase and to a second means for feeding 48B a second internal phase.

The first internal phase and the second internal phase have advantageously different compositions.

In the example shown in FIG. 5, the pipes 34A, 34B respectively open by downstream openings 60A, 60B that are transverse relative to the vertical axis AA' of the internal tube 52. The openings 60A, 60B are advantageously located opposite each other.

In particular, in the example shown in FIG. 5, the pipes 34A, 34B open into the upstream portion 70 perpendicular to the axis of circulation of the intermediate phase in the upstream portion 70.

Thus, in the method implemented by means of using the installation described in FIG. 5, the step of forming internal drops involves the formation of two respective trains of internal drops 20A, 20B containing respectively the first internal phase and the second internal phase.

The trains of drops 20A, 20B then circulate in the intermediate phase through the internal tube 52 up to the opening for formation of drops 56.

Then, least one first internal drop 20A formed from the first internal phase and at least one intermediate drop 20B formed from the second internal phase are introduced into an intermediate drop 18 being formed, to form a liquid body 35 as illustrated in FIG. 5.

The liquid body 35 forms, after its contact with the gelation bath 42, a capsule 12.

The capsule 12 comprises a shell 16 as previously described here above, an intermediate drop 18, at least one internal drop 20A containing the first internal phase and at least one internal drop 20B containing the second internal phase, the drops 20A, 20B being placed in the intermediate drop 18. In the particular example shown in FIG. 5, each capsule 12 includes two drops 20A and two drops 20B.

It should be noted that the number of internal drops 20A, 20B in each capsule is identical.

Figure 6:
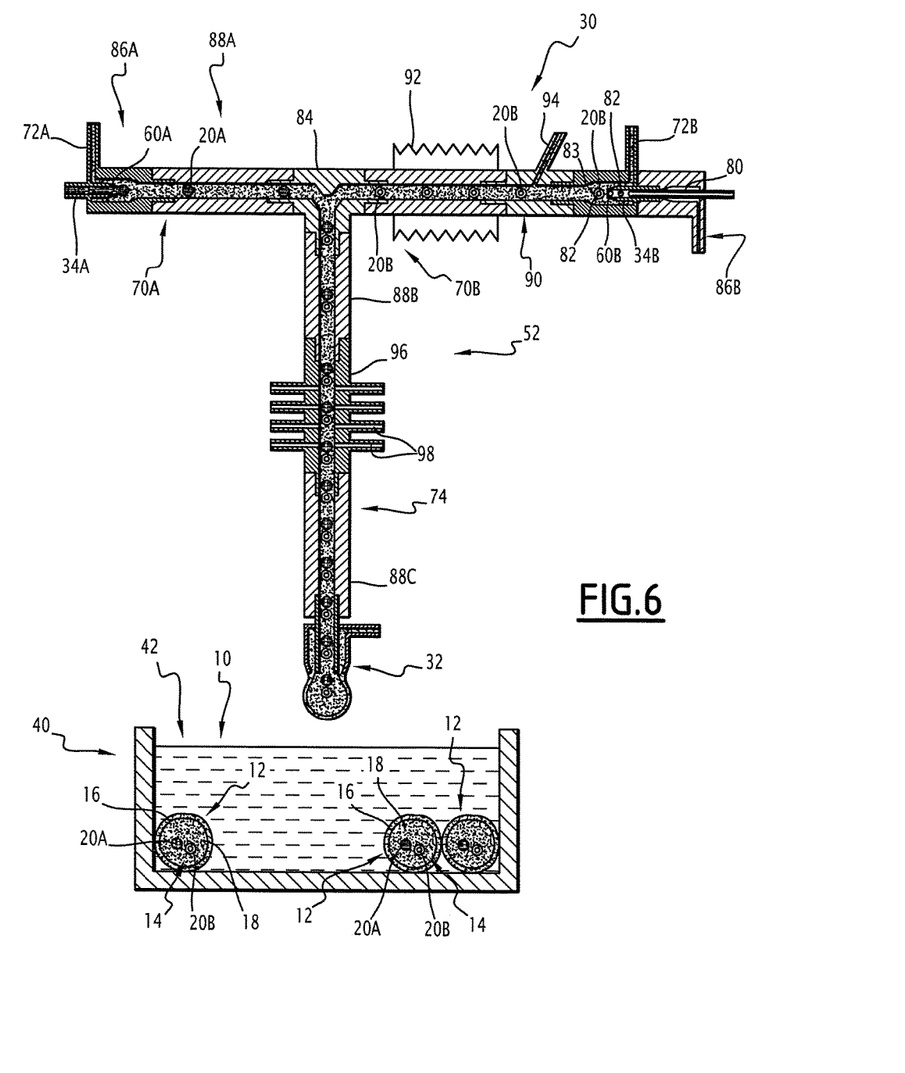
FIG. 6 is a view similar to FIG. 1 of a sixth apparatus for forming a sixth set of capsules according to the invention.

Another apparatus 30 is shown in FIG. 6. Unlike the apparatus 30 shown in FIG. 5, the internal tube 52 in which circulates the intermediate phase has two upstream portions 70A, 70B which converge in the downstream portion 72. Each upstream portion 70A, 70B includes a respective injection pipe 34A, 34B for the formation of internal drops 20A, 20B.

Each of the upstream portions 70A, 70B has an upstream inlet 72A, 72B for injection of the intermediate phase.

In this example, the internal pipes 34A, 34B each have a downstream opening 60A, 60B which opens downstream of the upstream inlet 72A, 72B.

Moreover, in the example shown in FIG. 6, the internal pipe 34B is provided with an internal tubing 80 for injecting a third internal phase, which is disposed in the internal pipe 34B.

The internal tubing 80 opens upstream of the opening 60A. It thus allows the formation of droplets of the third internal phase within the second internal phase. Thus, internal drops 20B formed at the outlet 60B comprises a nucleus 82 of the third internal phase and a shell of the second internal phase 83.

The upstream portions 70A, 70B converge in the downstream portion 74 within a mixing module 84 forming a connection.

In the example shown in FIG. 6, the apparatus 30 is also modular. It thus advantageously comprises, from upstream to downstream in the first portion 70A, a module 86A for formation of internal drops 20A and a module 88A for connection connected to the module 84 for mixing.

The apparatus 30 further comprises in the second portion 70B a module 90 for injection of a reagent, disposed downstream of a module for formation of drops 86B, and a reactor module 92, disposed downstream of the injection module 90 and connected to the mixing module 84.

The injection module 90 includes an pipe 93 for injecting the reactant product, the pipe 93 opens into a flow passage of the intermediate phase upstream of the reactor module 92.

The reactor module 92 is capable of triggering a chemical reaction in the intermediate phase or in the drops 20B. It comprises for example means for heating or means for cooling of the intermediate phase, the means for exposure of the intermediate phase to a light of a particular wavelength, such as Ultra Violet or Infra Red light or other means of reaction.

The downstream portion 74 has, from upstream to downstream, a connection module 88B, a module 96 for concentration or dilution and another module for connection 88C. It also includes a module for deposition of the film 36 of solution 38 on the intermediate drops of 38 having the double wall 32.

The connection module 88B is placed at the outlet of the mixing module 84.

The concentration/dilution module 90 has nozzles 98 for injecting or withdrawing from the intermediate phase out of the circulation flow passage of the intermediate phase in order to adapt the dilution of internal drops 20A, 20B in the intermediate phase.

It should be noted that the particular structure of the modules in FIG. 6 may be changed. Thus, the reaction module 92 and the injection module 90 may be disposed in the downstream portion 70 and the concentration/dilution module 92 can be arranged in one of the upstream portions 70A, 70B.

Moreover, when only one single type of internal drops 20 is placed in each external drop 18, the device 30 may include a single upstream portion 70, the reactor module 92 and the injection module 90 being then placed either in the upstream portion 70 or in the downstream portion 72.

The method for the formation of capsules 12 by means of using the apparatus 30 shown in FIG. 6 will now be described.

As previously described above, the first drops 20A and second drops 20B are respectively formed at the outlet of the internal pipes 34A, 34B. Thus, a train of first drops 20A and a train of second drops 20B being respectively circulate in the first upstream portion 70A and in the second upstream portion 70B, within the intermediate phase.

Then the first drops 20A and the second drops 20B mix together in the module 84 in order to form a train of internal drops 20A, 20B having alternating drops 20A and drops 20B.

The drops 20A, 20B then circulate in the downstream portion 74 up to the opening 56 where they are introduced into an external drop 18.

As previously described above, the external drop 18 containing at least one internal drop 20A and at least one internal drop 20B is coated with a film 36 of solution 38 so as to form a liquid body 35. The body 35 is detached from the opening 56 and falls by gravity through a volume of air into the gelation bath 42.

The capsules 12 thus obtained therefore comprise a shell 14, an internal drop 20A and an internal drop 20B within an external drop 18.

Moreover, in the specific method described in FIG. 6, the third internal phase 80 is injected into the second internal phase by way of the internal tubing 80 in order to form droplets of internal phase 82 surrounded by a shell 83 of second internal phase.

Moreover, the reagent injected through the pipe 94 is fed into the reactor module 92 around drops 20B. A chemical reaction is then conducted within the reactor module 92 that is, in the intermediate phase, that is in the shell 83 of second internal phase of the droplets 82.

Furthermore, a calibrated intermediate phase flow may be added by way of at least one nozzle 98 in the concentration/dilution module 96 in order to reduce the concentration of internal drops 20A, 20B in the intermediate phase. Alternatively, the intermediate phase can be removed through at least one nozzle 98 so as to increase the concentration in internal drops 20A, 20B in the intermediate phase.

In a variant of the capsules 12, each first drop 20A contains a first product capable of reacting with a second product contained in the second drop 20B. Thus, as the capsule 12 is intact, the first product remains confined away from the second product in the intermediate phase. Once the shell 16, is broken the first product may come into contact with the second product.

As has been noted above, the setting of different flow rates of fluids injected by the feeding means 44 to 48 makes it possible to adjust at the same time the size of the capsules 10, the relative thickness of the shell 16 with respect to the core 14, and the number of internal drops 20 in the external drop 18.

Figure 7:
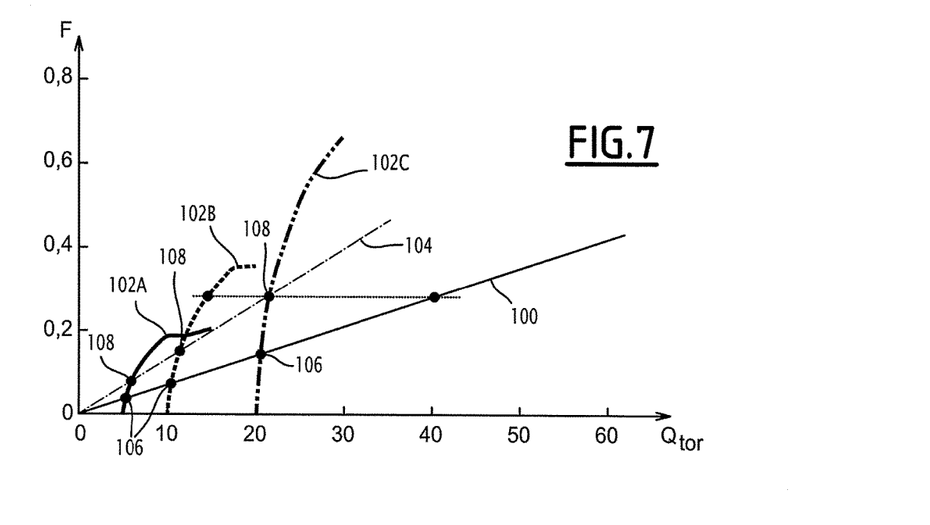
FIG. 7 is a graph illustrating the possibilities of flow control in the implementation of the processes for the manufacture of series of capsules according to the invention.

In the latter case, as shown in FIG. 7, it is possible to draw a curve 100 illustrating the frequency F of formation of external drops 18 containing internal drops 20 based on the total flow rate $Q_{TOT}$ injected by the means 44, 46, 48.

With reference to the apparatus shown in FIG. 2 or 3, the curves 102A, 102B, 102C for their part represent the frequency of formation of the internal drops 20 according to the flow rate of the intermediate phase injected by the upstream injection inlet 72. Thus, in order to form capsules 12 each comprising an external drop 18 provided with one single internal drop 20, it is possible to be placed at the intersections 106 between the curves 102A, 102B, 102C and the curve 100.

Moreover, one curve 104 representing an integer N times the frequency of formation of intermediate drops 18 represented on the curve 100 may be calculated.

In order to obtain a number N of internal drops 20 in each external drop 18, it is enough to be placed at the intersection of the curve 104 and each of the curves 102A, 102B, 102C.

Alternatively, from a point 108 on one of the curves 102A, 102B, 102C, it is possible in the apparatus of FIG. 3 to inject the intermediate phase by means of the downstream inlet 74 in order to dilute the internal drops and reach point B corresponding to the formation of N internal drops per intermediate drops 18.

The curves 100 and 102A to 102C can be established for each apparatus 30, according to each internal phase, intermediate phase and external phase in order to control the structure of each capsule 12.

In another variant, each internal drop 20 may include a plurality of levels of internal drops, as has been partially described in FIG. 6.

In another variant, is possible to control in an active manner the frequency of formation of internal drops 20A, 20B, depending on the frequency of formation of the external drops 18. This control can be done in particular by the use of solenoid valves, for controlling the or each rate of injection of the internal phase, and eventually for stopping the injection of internal phase. It is also possible to use pressure pulses to control the formation of internal drops 20 or controlled perturbations to trigger the formation of different drops.

Exemplary compositions of internal phase, intermediate phase, of polyelectrolyte solution for the implementation of formation of the series 10 of capsules 12 according to the invention are described in the tables below.

EXAMPLE 1

| Internal Phase | | | | |
|---|---|---|---|---|
| Flow rate (ml/hr/nozzle) | 0.25 | | % mass | |
| Ingredient | % mass | function | Core 14 | Capsule 12 |
| Jojoba Oil | 99% | solvent | 1.17% | 1.06% |
| red coloring | 1% | dye | 0.01% | 0.01% |

| Intermediate phase | | | | |
|---|---|---|---|---|
| Flow rate (ml/hr/nozzle) | | | % mass | |
| Ingredient % | % mass | function | Core 14 | Capsule 12 |
| Water | 98.0% | solvent | 96.85% | 87.57% |
| Carrageenan | 2% | thickener | 1.98% | 1.79% |

| Polyelectrolyte Solution | | | | |
|---|---|---|---|---|
| Flow rate (ml/hr/nozzle) | 2.25 | | % mass | |
| Ingredient % | % mass | function | Core 14 | Capsule 12 |
| Water | 97.9% | solvent | — | 9.37% |
| sodium alginate | 1% | gelling agent | — | 0.19% |
| sodium dodecyl sulfate | | surfactant | — | 0.01% |

EXAMPLE 2

| Internal Phase | | | | |
|---|---|---|---|---|
| Flow rate (ml/hr/nozzle) | 0.25 | | % mass | |
| Ingredient % | % mass | function | Core 14 | Capsule 12 |
| Jojoba Oil | 99% | solvent | 5.75% | 5.15% |
| red coloring | 1% | dye | 0.05% | 0.04% |

| Intermediate phase | | | | |
|---|---|---|---|---|
| Flow rate (ml/hr/nozzle) | 32.5 | | % mass | |
| Ingredient % | % mass | function | Core 14 | Capsule 12 |
| Water | 98.0% | solvent | 93.26% | 83.57% |
| sodium hyaluronate | 2% | thickener | 0.94% | 0.84% |

| Polyelectrolyte solution | | | | |
|---|---|---|---|---|
| Flow rate (ml/hr/nozzle) | 4 | | % mass | |
| Ingredient | % mass | function | Core 14 | Capsule 12 |
| Water | 97.9% | solvent | — | 10.17% |
| Sodium alginate | 2.0% | gelling agent | — | 0.21% |
| sodium dodecyl sulfate | 0.1% | Surfactant | — | 0.01% |

EXAMPLE 3

| Internal phase | | | | |
|---|---|---|---|---|
| flow rate (ml/hr/nozzle) | 2 | | % mass | |
| Ingredient | % mass | function | Core 14 | Capsule 12 |
| Jojoba oil | 99% | solvent | 5.75% | 5.15% |
| Red Dye | 1% | dye | 0.05% | 0.04% |

| Intermediate Phase | | | | |
|---|---|---|---|---|
| Flow rate (ml/hr/nozzle) | 32.5 | | % mass | |
| Ingredient % | % mass | function | Core 14 | Capsule 12 |
| Water | 99.0% | solvent | 3.26% | 83.57% |
| sodium hyaluronate | 1.0% | thickener | 0.94% | 0.84% |

EXAMPLE 4

Internal Phase

| Flow rate (ml/hr/nozzle) | 2 | | | % mass |
|---|---|---|---|---|
| Ingredient | % mass | function | Core 14 | Capsule 12 |
| Jojoba Oil | 99% | solvent | 10.84% | 9.75% |
| Red colouring | 1% | dye | 0.09% | 0.08% |

Intermediate phase

| Flow rate (ml/hr/nozzle) | 16.3 | | | % mass |
|---|---|---|---|---|
| Ingredient | % mass | function | Core 14 | Capsule 12 |
| Water | 99.0% | solvent | 88.18% | 79.34% |
| sodium hyaluronate | 1.0% | thickener | 0.89% | 0.80% | polyelectrolyte solution

| Flow rate (ml/hr/nozzle) | 2.04 | | | % mass |
|---|---|---|---|---|
| Ingredient | % mass | function | Core 14 | Capsule 12 |
| Water | 97.9% | solvent | — | 9.81% |
| Sodium alginate | 2.0% | gelling agent | — | 0.20% |
| Sodium dodecyl sulfate, | 0.1% | surfactant | — | 0.01% |

Polyelectrolyte solution

| Flow rate (ml/hr/nozzle) | 4 | | | % mass |
|---|---|---|---|---|
| Ingredient | % mass | function | Core 14 | Capsule 12 |
| Water | 97.9% | solvent | — | 10.17% |
| Sodium alginate | 2.0% | gelling agent | — | 0.21% |
| sodium dodecyl sulfate, | 0.1% | surfactant | — | 0.01% |

EXAMPLE 5

Internal Phase

| Flow rate (ml/hr/nozzle) | 1 | | | % mass |
|---|---|---|---|---|
| Ingredient | % mass | function | Core 14 | Capsule 12 |
| Jojoba oil | 99% | solvent | 4.51% | 4.09% |
| red coloring | 1% | dye | 0.04% | 0.03% |

Internal Phase 2

| Flow rate (ml/hr/nozzle) | 1 | | | % mass |
|---|---|---|---|---|
| Ingredient | % mass | function | Core 14 | Capsule 12 |
| Jojoba Oil | 99% | solvent | 4.51% | 4.09% |
| red coloring | 1% | dye | 0.04% | 1.73% |

Intermediate phase

| Flow rate (ml/hr/nozzle) | 21 | | | % mass |
|---|---|---|---|---|
| Ingredient | % mass | function | Core 14 | Capsule 12 |
| Water | 98.0% | solvent | 93.55% | 84.87% |
| Carrageenan | 2.0% | thickener | 1.91% | 1.73% |

Polyelectrolyte solution

| Flow rate (ml/hr/nozzle) | 2.25 | | | % mass |
|---|---|---|---|---|
| Ingredient | % mass | function | Core 14 | Capsule 12 |
| Water | 97.9% | solvent | — | 9.08% |
| Sodium alginate | 2.0% | gelling agent | — | 0.19% |
| sodium dodecyl sulfate | 0.1% | Surfactant | — | 0.01% |

In a particular embodiment, each capsule 12 of the series 10 has an internal liquid drop 20 that is made with a base of an internal aqueous phase. The internal phase advantageously comprises a hydrophilic cosmetic active agent such as an antioxidant active ingredient. The intermediate drop 18 is made with a base of an oily intermediate phase, in particular containing a silicone polymer, such as a silicone-based copolymer in polydimethylsiloxane.

The mass content of crosspolymer solution is for example between 60% and 90%, and the mass content of polydimethylsiloxane for example between 40% and 10%.

The intermediate drop 18 is advantageously viscous or gelled. Thus, the internal drop 20 is centered relative to the intermediate drop 18.

Each capsule 12 advantageously includes a single internal drop 20, the internal drop 20 having a volume greater than 0.5% and advantageously less than 60% of the volume of the core Advantageously, the internal drop 20 includes more than 90% by weight of cosmetic active ingredient.

The intermediate drop 18, in combination with the gelled shell 16 acts as a barrier to the diffusion of the cosmetic active ingredient out of the internal drop 20 through the intermediate drop 18 and the gelled shell 16.

In another embodiment, the intermediate drop 18 contains solid particles such as particles of pearl.

It should be noted more generally that the internal drop 20 like the intermediate drop 18 are without surfactant or a solvent containing alcohol.

As can be seen in particular in FIG. 1, the process of manufacturing the capsules 12 of the series 10 includes the formation of a substantially spherical liquid body 35 then the detaching of the body 35 so as to let it fall into a gelation bath 42 by gravity, through a volume of air, prior to forming another body 35. The method of formation of capsules 12 is effected drop by drop and not in a continuous manner by separating a jet.

The invention claimed is:

1. A method for manufacturing a series of capsules, each capsule comprising a liquid core and a gelled shell completely encapsulating the liquid core, the method comprising of the following steps:

separate conveying in a double wall of an intermediate phase intended to form the liquid core and a first solution containing a polyelectrolyte liquid capable of gelling intended for forming the gelled shell;

forming at the outlet of the double wall of a series of liquid bodies including one drop of intermediate phase coated with a peripheral film formed by the first solution, the first solution containing at least one surfactant prior to its contact with the intermediate phase;

detaching each liquid body away from the double wall and falling of each liquid body in a volume of air;

immersing each liquid body into a gelling solution containing a reagent capable of reacting with the polyelectrolyte of the film in order to make it pass from a liquid state to a gelled state and thereby form the gelled shell;

recovering the capsules formed with a ratio of the volume of the core to the volume of the shell being greater than 2;

the method comprising a step of forming at least one internal macroscopic drop of one internal phase in the intermediate phase, each liquid body formed at the outlet of the double wall comprising one internal macroscopic drop of an internal phase disposed in the intermediate phase;

wherein the intermediate phase is aqueous and the internal phase is oily.

2. The method of claim 1 wherein an internal pipe conveys the internal phase in an internal tube, the internal pipe defining an opening and the internal tube defining an opening for drop formation;

wherein the internal pipe is withdrawn in the internal tube such that the distance taken along the axis between the opening of the internal pipe and the opening for drop formation is between 10 times and 1000 times the diameter of the internal pipe taken at a downstream opening.

3. The method of claim 1, wherein each intermediate drop of the intermediate phase formed at the outlet of the double wall comprises at least two internal drops placed in the intermediate phase.

4. The method of claim 1, wherein the step of formation includes injection of the internal phase in a current of the intermediate phase flowing in the double wall so as to form internal macroscopic drops.

5. The method of claim 1, wherein the injection of the internal phase is achieved through an internal duct arranged in the double wall, the internal duct opening advantageously at exit of the double wall.

6. The method of claim 1, comprising the adjusting of the rate of injection of the internal phase in the intermediate phase relative to the rate of injection of the intermediate phase in order to adjust the number of internal macroscopic drops present in each intermediate drop formed at the outlet of the double wall.

7. The method of claim 1, wherein the step of formation includes injection of the internal phase in a current of the intermediate phase flowing in the double wall so as to form internal macroscopic drops.

8. The method of claim 1, comprising the adjusting of the rate of injection of the internal phase in the intermediate phase relative to the rate of injection of the intermediate phase in order to adjust the number of internal macroscopic drops present in each intermediate drop formed at the outlet of the double wall.

9. The method of claim 1, wherein the viscosity of the internal phase forming the internal macroscopic drop is less than 10% of the viscosity of the intermediate phase during the formation of the internal macroscopic drop.

* * * * *